United States Patent [19]

Cepuritis

[11] 3,967,622
[45] July 6, 1976

[54] DISPOSABLE DIAPER WITH DIVARICATED ADHESIVE TABS

[75] Inventor: Talivaldis Cepuritis, Kenilworth, Ill.

[73] Assignee: Johnson & Johnson, New Brunswick, N.J.

[22] Filed: May 7, 1975

[21] Appl. No.: 575,280

[52] U.S. Cl. ............................................. 128/287
[51] Int. Cl.² ..................................... A41B 13/02
[58] Field of Search ......... 128/278, 284, 287, 290 R

[56] References Cited
UNITED STATES PATENTS

| | | | |
|---|---|---|---|
| 3,776,234 | 12/1973 | Hoey | 128/287 |
| 3,893,460 | 7/1975 | Kamami | 128/284 X |

Primary Examiner—Lawrence Charles

[57] ABSTRACT

A disposable diaper having an inside surface for direction toward an infant and an outside surface is provided with adhesive tabs, each tab having an adhesive coating on one face thereof. Each tab has a first end portion which is permanently attached to a marginal portion of the diaper outside surface by means of the adhesive coating, and an opposite end portion which is divided longitudinally into a central strip and a pair of marginal strips flanking the central strip. The marginal strips are permanently attached to a marginal portion of the diaper inside surface by means of the adhesive coating. A release layer is releasably adhered to the adhesive coating on the central strip and removable therefrom, whereby the central strip provides a securement means for fastening the diaper about an infant.

11 Claims, 11 Drawing Figures

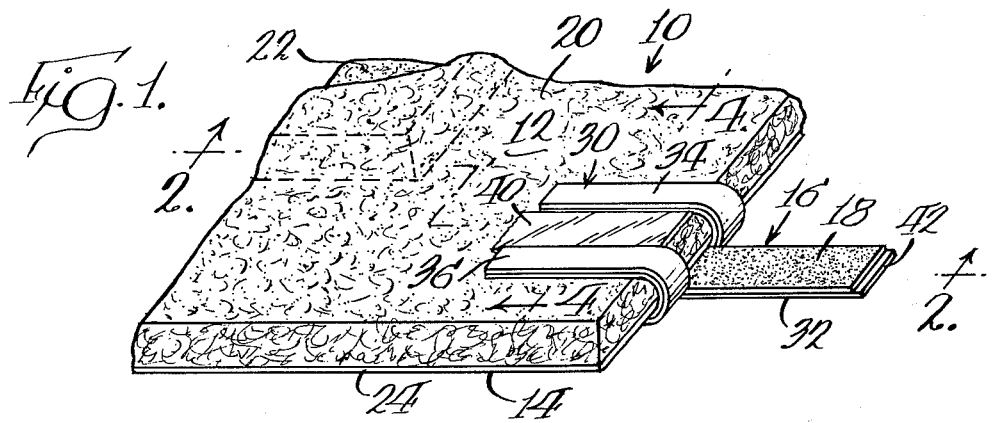
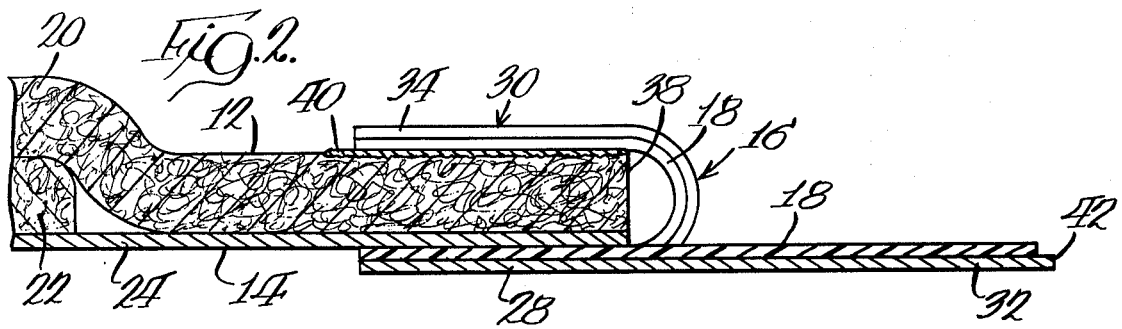
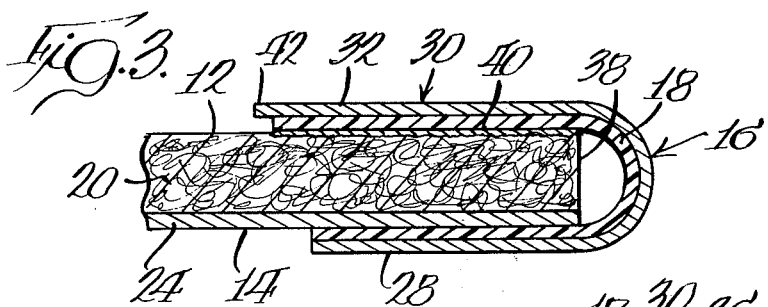
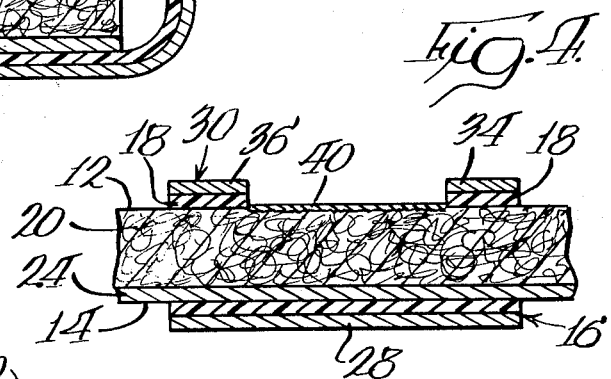
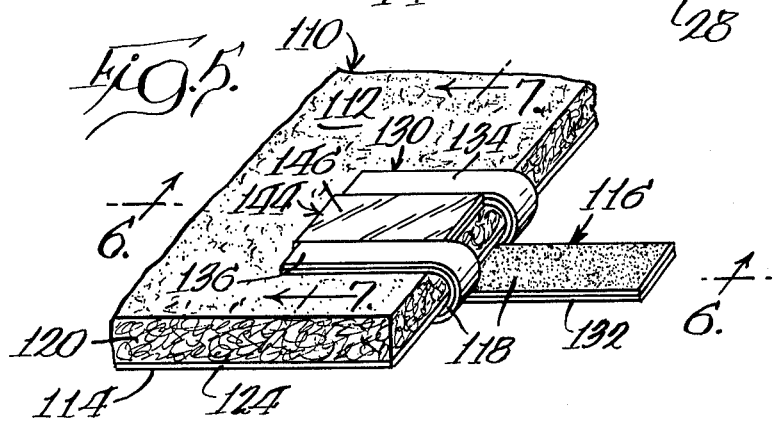

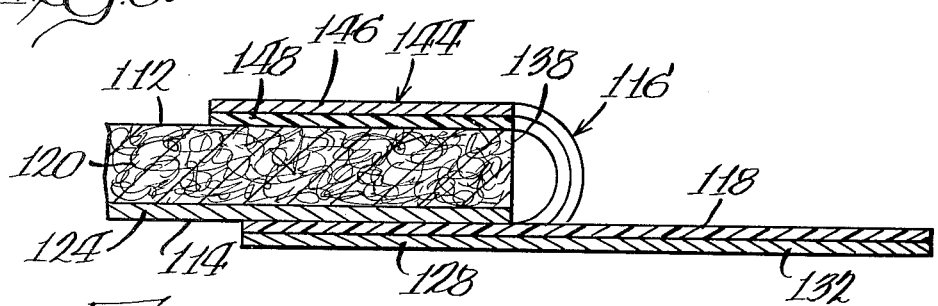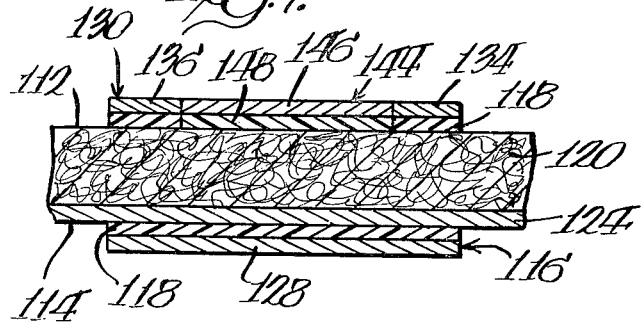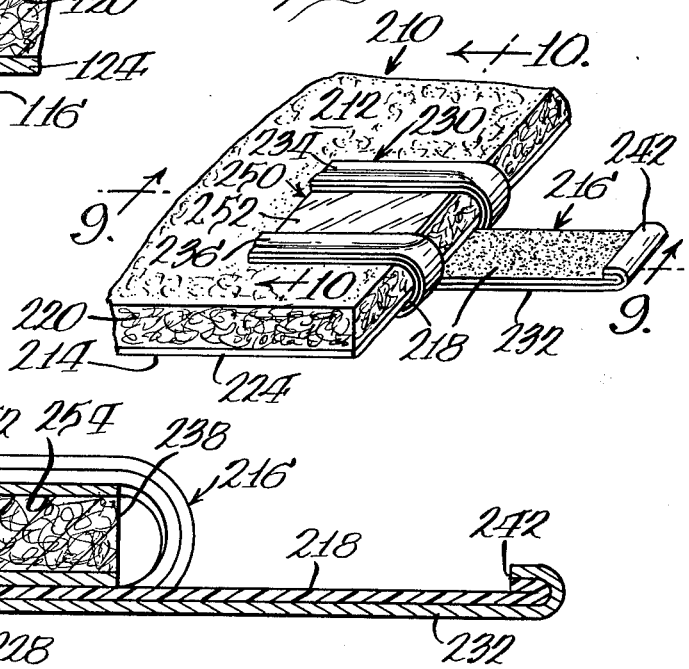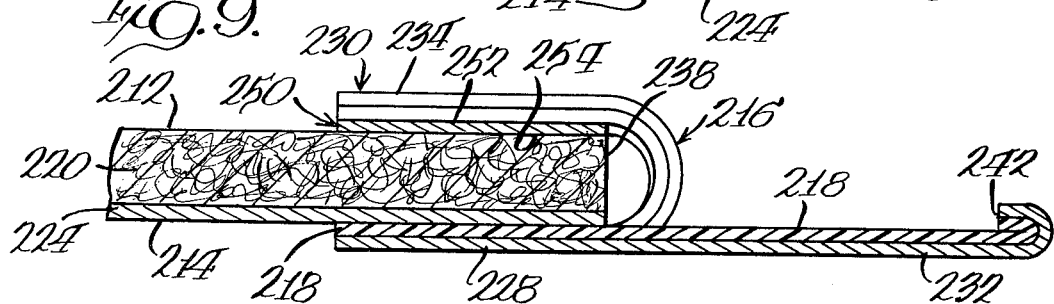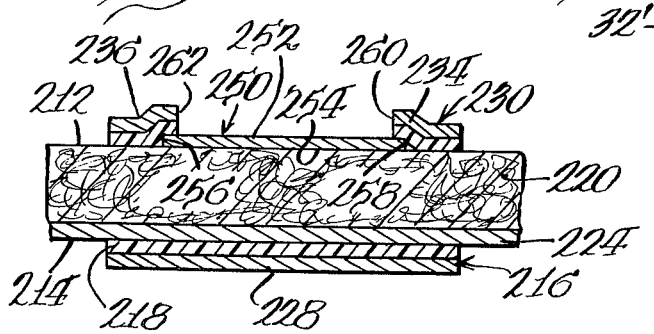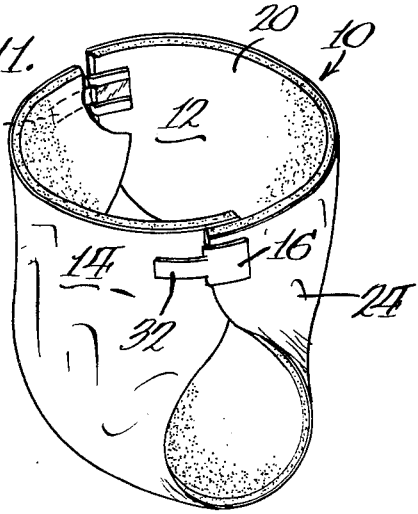

DISPOSABLE DIAPER WITH DIVARICATED ADHESIVE TABS

BACKGROUND OF THE INVENTION

This invention relates to disposable diapers. More particularly, this invention relates to disposable diapers adapted to be secured in place by adhesive tabs.

Disposable diapers provide substantial advantages in convenience over diapers intended to be laundered and reused, particularly when they are used away from home. In recent years, many different disposable diapers have been proposed and some have been successful in the marketplace. Typical disposable diaper structures comprise a moisture-retaining layer of high liquid-holding capacity and a moisture-impervious backing sheet, generally made of a plastic film such as polyethylene film or the like. Typical disposable diaper structures are shown in U.S. Pat. No. 3,612,055 to Mesek et al. and in U.S. Pat. No. Re. 26,151 to Ducan et al.

As may be seen from the above-cited patents, it is desirable to obviate the problems that are inherent in closure systems which utilize extraneous fasteners such as safety pins, snaps and zippers. To this end adhesive closure systems have presented acceptable solutions.

In order to protect the adhesive surfaces of the tape tabs, usually a cover strip having a release surface is applied over these adhesive surfaces for subsequent removal when the diaper is about to be used. However, such tabs usually project beyond the confines of the diaper to a considerable extent and interfere with the efficient manufacture and packaging of the diaper.

In an attempt to solve the foregoing problems, U.S. Pat. No. 3,776,234 to Hoey proposes to fold the tab over on itself at the diaper's edge and to adhesively attach a portion of the folded-over tab segment to an inwardly-folded margin of the diaper backing sheet in order to keep the tab flat against the diaper and thus from interfering with the manufacturing machinery and with the subsequent folding and packaging operations. This requires that the edge of the diaper backing sheet be folded over to present an attachment surface at the front or inside face of the diaper, and a relatively involved tab design is necessary for this purpose. Also, undesirable tearing of the diaper facing fabric may result if such a tab is inadvertently adhesively attached to the facing fabric of the diaper during manufacture.

U.S. Pat. No. 3,750,669 to DeLuca shows a fastening tape provided with an adhesive end portion which extends beyond a cover strip for the tape and which is attached to a diaper inner covering or facing. However, such an adhesive end portion, when attached to a fibrous, non-woven facing fabric is likely to tear the facing fabric upon separation therefrom.

U.S. Pat. No. 3,646,937 to Gellert shows a fastening tab which is provided with a release surface permanently bonded to the inside surface of the diaper. One of the problems of the Gellert arrangement, as well as all of the other above-cited patents, is that the adhesive tape fasteners are permanently attached to only one surface of the diaper, generally the outside surface of the backing sheet, and thus all of the force exerted on the tape fastener during securement or as the infant moves about is directed to the joint between one end of the tape fastener and the diaper backing sheet.

The tape fastener in U.S Pat. No. 3,848,594 to Buell is attached to both the front and back surfaces of the diaper, but has the disadvantage in that each tape fastener is comprised of at least two separate tape segments which are joined together, thereby adding complexities and expense to the manufacturing process.

The adhesive fastener disclosed in U.S. Pat. No. 3,833,456 to Reed et al. can also be attached to both the front and back surfaces of a substrate. This fastener has the disadvantages, however, of comprising two coextensive webs with each web having an adhesive coating extending along substantially all of one face. The lower web has a release coating along a portion of the opposite face so that a portion of the adhesive coating on the upper web is releasably secured thereto and the rest of the adhesive coating bonds the two webs together. Since two webs are required, the fastener is bulky in the folded configuration, and is relatively expensive to manufacture.

SUMMARY OF THE INVENTION

In this invention, a divaricated adhesive tab is used to secure the diaper on an infant and is made of a single tape segment having a pressure sensitive adhesive coating on one face thereof. A first end portion of the tape segment is permanently attached to the diaper backing sheet, and the opposite end portion is folded over a longitudinal edge of the diaper and is divided longitudinally into a central strip and two marginal strips. The marginal strips are permanently attached to the diaper inside surface by means of the adhesive coating. A release surface is provided between the central strip and the diaper inside surface, and the central strip is releasably adhered thereto. The release surface may comprise a release coating printed or otherwise deposited on a portion of the diaper inside surface, a release strip having a release coating on one face thereof and an adhesive coating on the opposite face by means of which the release strip is adhered to the diaper, a release strip having a release coated and wider than the central strip but narrower than the opposite end portion of the tab so that the marginal strips anchor the release strip to the diaper inside surface, or other suitable means for releasably adhering the central strip to the diaper.

The divaricated tape tabs of the present invention are secured to opposite surfaces of the diaper yet remain flat against the diaper when in the folded configuration and will not interfere with the manufacturing machinery and the subsequent folding and packaging operations. Additional features of this invention include the utilization of an integral adhesive tab which is inexpensive and simple to manufacture, and permanent attachment of the tab to both the diaper backing sheet and the diaper inside surface so that when stress imposed on the central strip which fastens the diaper causes the diaper backing sheet to yield or stretch, a portion of the stress is transmitted to the inside surface of the diaper thereby reducing the possibility of premature rupture of the backing sheet.

BRIEF DESCRIPTION OF THE DRAWINGS

FIG. 1 is a fragmentary perspective view of an open unfolded diaper in accordance with one embodiment of the invention;

FIG. 2 is an enlarged cross-sectional view of the diaper of FIG. 1 taken along plane 2—2;

FIG. 3 is an enlarged cross-sectional view similar to FIG. 2 and illustrating the tape tab in its folded over closed position;

FIG. 4 is an enlarged cross-sectional view of the diaper of FIG. 1 taken along plane 4—4;

FIG. 5 is a fragmentary perspective view similar to FIG. 1 illustrating an alternate embodiment of the invention;

FIG. 6 is an enlarged fragmentary cross-sectional view of the diaper of FIG. 5 taken along plane 6—6;

FIG. 7 is an enlarged fragmentary cross-sectional view of the diaper of FIG. 5 taken along plane 7—7;

FIG. 8 is a fragmentary cross-sectional view similar to FIGS. 1 and 5 illustrating another embodiment of the invention;

FIG. 9 is an enlarged fragmentary cross-sectional view of the diaper of FIG. 8 taken along plane 9—9;

FIG. 10 is an enlarged fragmentary cross-sectional view of the diaper of FIG. 8 taken along plane 10—10; and FIG. 11 is a perspective view of the diaper of FIG. 1 in a configuration assumed by the diaper when placed about an infant.

DESCRIPTION OF THE PREFERRED EMBODIMENTS

In the following description, two digit numerals are used to refer to the embodiment illustrated in FIGS. 1–4 and 11, three digit numerals 100–199 are used to refer to the embodiment illustrated in FIGS. 5–7, and three digit numerals 200–299 are used to refer to the embodiment illustrated in FIGS. 8–10. The same last two digits in each numeral designate similar elements in the various embodiments.

Disposable diaper 10, illustrated in FIGS. 1 and 11, is of substantially quadrilateral configuration and presents inside surface 12 for direction toward an infant and outside surface 14 for direction away from the infant. Adhesive tabs such as tab 16 are attached to diaper 10 for securing diaper 10 about an infant. Tab 16 is provided with a pressure-sensitive adhesive coating 18 extending over substantially all of one face thereof.

Referring to FIGS. 1, 2 and 11, diaper 10 comprises a moisture-retaining layer made of moisture-pervious facing sheet 20 which defines the diaper inside surface 12, overlying the absorbent pad 22, and backing sheet 24 which is made of a moisture-pervious material and defines the diaper outside surface 14. Absorbent pad 22 is somewhat smaller than backing sheet 24 and is centrally disposed thereon; however, absorbent pad 22 can be made co-extensive with backing sheet 24, if desired. Facing sheet 20 is substantially coextensive with backing sheet 24. Both facing sheets 20 and pad 22 can be anchored to backing sheet 24 by means of adhesive beads, glue spots, or in any other convenient manner. For example, if backing sheet 24 is made of a thermoplastic material, facing sheet 20 and pad 22 can be attached thereto by heat bonding.

As illustrated in FIGS. 1–4, adhesive tab 16 has fixed end portion 28 which is permanently attached by means of adhesive coating 18 to backing sheet 24 on the diaper outside surface 14 at a marginal location thereon, and an opposite end portion 30 which is divided longitudinally into at least three separate strips comprising a central strip 32 and a pair of marginal strips 34 and 36 on opposite sides of central strip 32. Marginal strips 34 and 36 flank the central strip 32 and are permanently attached to facing sheet 20 on the diaper inside surface 12 at a marginal location thereon by means of adhesive coating 18. Strips 32, 34 and 36 are formed by longitudinally cutting opposite end portion 30 of tab 16 into the desired number of strips.

Referring to FIGS. 2 and 3, tab 16 is folded about longitudinal edge 38 of diaper 10, and end portions 28 and 30 of tab 16 preferably are about equal in length. Central strip 32 provides a securement means for fastening the diaper about an infant and can be moved from the closed position of FIG. 3 to the open position of FIG. 2.

If the backing sheet is a thermoplastic web, fixed end 28 can also be attached to backing sheet 24 by heat bonding in which case adhesive coating 18 is coextensive only with opposite end 30.

A release means providing a release surface or layer is provided for releasable adhesion to adhesive coating 18 carried on central strip 32. This invention contemplates various embodiments in which a release surface or layer is provided between adhesive coating 18 on central strip 32 and diaper inside surface 12 which is juxtaposed to central strip 32 when the central strip is in the folded over closed position. In the embodiment illustrated in FIGS. 1–4, release layer 40 is a surface coating on a portion of the diaper inside surface 12. Release layer 40 is positioned between marginal strips 34 and 36 and is preferably about the same width as central strip 32. Preferably the release layer 40 comprises a silicone release compound and is at least as long as central strip 32. Thus, a user can grasp the distal end 42 of central strip 32 and pull the central strip outwardly from the closed position illustrated in FIG. 3 to the open position illustrated in FIG. 2 so as to expose adhesive coating 18, whereby central strip 32 may be employed to secure diaper 10 about an infant.

When central strip 32 is superposed on the diaper inside surface 12, it is important that the adhesive coating 18 on central strip 32 avoids contact with any portion of the diaper inside surface 12 or the adjacent marginal strips 34 and 36 so that central strip 32 is easily releasable from release layer 40 to secure the diaper about an infant. Since central strip 32 is preferably formed from an integral tape segment which is cut along a portion of the longitudinal length to provide strips 32, 34 and 36, central strip 32 does not overlap either of the marginal strips 34 and 36. Furthermore, release layer 40 extends between the inner edges 60 and 62 of marginal strips 34 and 36 and, desirably, is longer than central strip 32 to insure that the central strip will not contact the diaper inside surface 12.

In the embodiments illustrated in FIGS. 5–10, the release surface comprises a ribbon segment or release strip having a release coated surface on one face. The release strip is anchored to the diaper inside surface 12 between marginal strips 34 and 36 by means of an adhesive or the like. Referring specically to FIGS. 5–7, disposable diaper 110 is provided with a release strip 144 having a release coated surface on face 146 and an adhesive coating 148 on the opposite face by means of which release strip 144 is anchored to the diaper inside surface 112. Release strip 144 preferably is of about the same width as central strip 132 and is positioned between marginal strips 134 and 136.

Another embodiment is illustrated in FIGS. 8–10 wherein diaper 210 has release strip 250 having a release coated surface on face 252 which is directed in the same direction as diaper inside surface 212. Opposite face 254 of release strip 250 adjoins diaper inside surface 212. Release strip 250 has a width greater than the width of central strip 232 and less than the width of opposite end portion 230 of tab 216. As best illustrated in FIG. 10, marginal portions of release strip 250 adjacent to edges 256 and 258 thereof are disposed between the diaper inside surface 212 and the inner edge portions 260 and 262 of marginal strips 234 and 236. Marginal strips 234 and 236 are permanently attached to diaper inside surface 212 and to release strip 250 by means of adhesive coating 218. In this manner release strip 250 is anchored to diaper inside surface 212. However, the release strip can also be a separate piece which is removed and discarded when the diaper is prepared for use.

Various means can be provided to facilitate gripping the distal end 42 of central strip 32 in order to lift central strip 32 from the anchored release surface. As illustrated in FIGS. 1 and 5, release layer 40 or release strip 144 can have a longitudinal dimension greater than the length of central strip 32 to enable a user to more easily grasp distal end 42 of central strip 32. Alternatively, as illustrated in FIGS. 1 and 2, tab 16 can be provided with an extension adjacent the distal end 42 of central strip 32, with the extension projecting outwardly beyond adhesive coating 18. The extension provides a gripping means for removing central strip 32 from release layer 40 when fastening the diaper about an infant. In FIGS. 8–10, a terminal segment of distal end 242 is folded over upon itself so that adhesive coating 218 is juxtaposed to itself. Two or more of the above modifications may be simultaneously utilized to facilitate gripping the distal end of central strip 32.

Adhesive tabs suitable for the purposes of the present invention can be made from a wide variety of materials, provided that such materials are sufficiently flexible. Preferred materials for this purpose are polyalkylene webs such as polyethylene sheet, polypropylene sheet, and the like. Particularly preferred are webs which are oriented along the narrow dimension of the tab or webs which have filament reinforcements therein.

The pressure-sensitive adhesive layers such as adhesive coating 18 are provided by applying a coating of a pressure-sensitive adhesive composition known in the art to the appropriate surface of tab 16. The applied adhesive shall have good tack, good cohesive strength, good resistance to moisture and good resistance to aging. Illustrative of such adhesive compositions are mixtures of natural or synthetic rubber, zinc oxide, and various resins, also latices of natural or synthetic rubber, or water dispersions or acrylic tacky polymers or copolymers, and the like.

Release strips 144 and 250 can be made from smooth plastic film having a relatively non-adhering surface, from paper coated with a silicone release compound, or from similar release materials. A number of appropriate release coatings may be used with the present invention. Examples of such coatings are disclosed in U.S. Pat. No. 2,822,290 to Webber; U.S. Pat. No. 2,880,862 to Sermattei; and U.S. Pat. No. 2,985,554 to Dickard.

Several different types of facing materials may be used for diaper facing sheet 20. For example, facing sheet 20 may be made up of a mixture of fibers consisting predominantly of inexpensive short cellulosic fibers such as wood pulp fibers or cotton linters, in amounts of about 75% to about 98%, the balance being textile length fibers such as rayon as described in U.S. Pat. No. 3,663,348 to Liloia et al.

Facing sheet materials suitable for use in this invention can have fabric weights in the range of about 1 to 5 oz./yd.$^2$ and densities of less than 0.15 g./cc., generally in the range between 0.05 and 0.1 g./cc. The dry strength of the facing sheet for a fabric having a weight of about 1.5 oz./yd.$^2$ is at least 0.15 lbs./in. of width in the machine direction and at least 0.1 lbs./in. of width in the cross direction. Such fabrics have unusually good elongation, loft, softness, and drape characteristics in comparison to prior products incorporating any substantial amount of short fibers.

Facing sheet 20 may also be made of an apertured, nonwoven fabric which is formed, for example, in accordance with the teachings of commonly assigned U.S. Pat. Nos. 2,862,251; 3,081,514 and 3,081,515. Briefly, such fabrics are foraminous structures wherein groups or groupings of fibers have been rearranged from a fibrous nonwoven starting web into positions surrounding less dense fabric portions by passage of a fluid through the starting material. The fibers within the groupings are mechanically interlocked, and may be arranged into various patterns, as is well known by those skilled in the art. A suitable binder may be utilized to help retain the fibers in their rearranged locations, as is also well known by those skilled in the art. The fabric can be made of naturally occurring fibers, synthetic fibers, or blends thereof. Typical facing sheets made of a polyester type material can have a weight of about 0.75 oz./yd.$^2$.

In addition, facing sheet 20 can be formed of a non-apertured material, such as a nonwoven isotropic web, or the like. In all of the aforementioned facing materials, the material should be relatively hydrophobic so as to retard wicking within the facing layer.

Highly moisture-absorbent fibrous pad or batt 20, which usually is substantially rectangular in shape but smaller than the facing sheet and the backing sheet, can be formed in accordance with the teachings of U.S. Pat. No. 3,612,055 to Mesek et al. If desired, a highly moisture-absorbent layer can be provided substantially coextensive with backing sheet 24 and facing sheet 20.

A suitable backing sheet material for the diapers embodying the present invention can be an opaque polyethylene web about 0.001 inch thick. Another suitable material for this purpose is a polyethylene terephthalate web having a thickness of about 0.0005 inch. Typical disposable diapers which can be fitted with tab-type adhesive fasteners described hereinabove are shown in U.S. Pat. No. 3,612,055 to Mesek et al. and in U.S. Pat. No. 3,683,916 to Mesek et al. Other suitable disposable diaper structures which can be improved by the present tab-type fasteners are shown in U.S. Pat. No. Re. 26,151 to Duncan et al.

In use, a diaper equipped with the adhesive fasteners of the present invention is applied to the infant by laying out the diaper on a suitable flat surface and placing the infant thereon so that the waist-underlying end of the diaper is that having the fastener means. The other end of the diaper then extends downwardly between the infant's less. Next, the downwardly extending end of the diaper is brought up between the infant's legs to a position contiguous with the front of the infant's waist. The diaper is thereafter secured to the infant by placing the corners of the waist portion of the abdomen-covering end as far around the infant's waist as they will go and by bringing the corners of the underlying end of the diaper into an overlapping relationship with the aforementioned corners so that the diaper snugly encircles the infant's waist and provides a custom fit. The adhesive fasteners are then prepared for use by pulling central strips 32 and 32' away from their temporary engagement with release layer 40 on facing sheet 20, grasping the exposed central strips and pulling the central strips away from the release layer which is releasably adhered to the adhesive coating 18 on the central strips and removable therefrom. The tabs are then used to secure the diaper in the desired position by simply urging the pressure-sensitive adhesive surfaces in contact with the adjacent outer surface of the diaper. The applied diaper assumes the configuration illustrated in FIG. 11.

The foregoing description and the drawing are illustrative but are not to be taken as limiting. Still other variations and modifications are possible without departing from the spirit and scope of the present invention.

I claim:

1. A disposable diaper having an inside surface for direction toward an infant, a moisture-impervious backing sheet defining a diaper outside surface, and an adhesive tab means comprising:

an elongated tape segment provided with a pressure-sensitive adhesive coating on one face thereof and having first and second end portions, said first end portion of said tape segment being permanently attached by means of said adhesive coating to said outside surface at a marginal location thereon and said second end portion being divided longitudinally into at least three separate strips comprising a central strip and a pair of marginal strips on opposite sides of said central strip, said central strip providing securement means for fastening the diaper about said infant and said marginal strips being adhesively attached to said diaper inside surface at a marginal location thereon, and release means providing a release surface releasably adhered to the adhesive coating on said central strip and removable therefrom.

2. The disposable diaper as defined in claim 1 wherein said first and second end portions of said tape segment are about equal in length.

3. The disposable diaper as defined in claim 1 wherein said release means is anchored to said diaper inside surface between said marginal strips.

4. The disposable diaper as defined in claim 1 wherein said release means is a coating on a portion of said diaper inside surface.

5. The disposable diaper as defined in claim 4 wherein said release coating comprises a silicone release compound.

6. The disposable diaper as defined in claim 1 wherein said release means comprises a ribbon segment having a release coating on one face and adhesively affixed to the inside surface of the diaper.

7. The disposable diaper as defined in claim 6 wherein said ribbon segment is provided with a pressure sensitive adhesive coating on a face opposite the face bearing the release coating, and wherein said ribbon segment is permanently attached to said diaper inside surface by said adhesive coating.

8. The disposable diaper as defined in claim 6 wherein said ribbon segment has a width greater than the width of said central strip and less than the width of said second end portion of said tape segment, and wherein opposite edge portions of said ribbon segment are disposed between said diaper inside surface and adjacent edge portions of said marginal strips, and wherein said ribbon segment is attached to said diaper inside surface by said marginal strips.

9. The disposable diaper as defined in claim 1 wherein a segment of the distal end of said central strip is folded over to provide a gripping means for removing said central strip from said release surface when fastening said diaper about said infant.

10. The disposable diaper as defined in claim 1 wherein said release surface has a longitudinal dimension greater than said central strip to facilitate gripping said central strip for removing said central strip from said release surface when fastening said diaper about said infant.

11. The combination as defined in claim 1 wherein said tape segment is provided with an extension adjacent the distal end of said central strip, said extension projecting beyond said adhesive coating on said one face of said tape segment, whereby said extension provides a gripping means for removing said central strip from said release layer when fastening said diaper about said infant.

* * * * *